US00PP31908P2

(12) United States Plant Patent
Probst

(10) Patent No.: US PP31,908 P2
(45) Date of Patent: Jun. 23, 2020

(54) ***COREOPSIS* PLANT NAMED 'SWEET TART'**

(50) Latin Name: ***Coreopsis* hybrid**
Varietal Denomination: Sweet Tart

(71) Applicant: Darrell R Probst, Hubbardston, MA (US)

(72) Inventor: Darrell R Probst, Hubbardston, MA (US)

( * ) Notice: Subject to any disclaimer, the term of this patent is extended or adjusted under 35 U.S.C. 154(b) by 0 days.

(21) Appl. No.: 16/501,936

(22) Filed: Jul. 8, 2019

(51) Int. Cl.
*A01H 5/02* (2018.01)
*A01H 6/14* (2018.01)

(52) U.S. Cl.
USPC ..... Plt./417

(58) Field of Classification Search
USPC ..... Plt./263.1, 417
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of hybrid *Coreopsis* plant named 'Sweet Tart' that is characterized by its sturdy, well-branched plant habit reaching an average of 40 cm in height and 70 cm in width, its floriferous and long blooming season of nearly sterile inflorescences that do not require deadheading; bloom commences in early July and lasts until frost in Kensington, Conn., its medium sized inflorescences with ray florets that are vibrant raspberry rose in color with a small area of yellow at the base (insignificant eye zone), its resistance to powdery mildew (*Podosphaera macularis*) and leafspot (*Pseudomonas cichorii*) and its cold hardiness at least to U.S.D.A. Zone 5a.

2 Drawing Sheets

Botanical classification: *Coreopsis* hybrid.
Variety denomination: 'Sweet Tart'.

CROSS REFERENCE TO A RELATED APPLICATIONS

This application is related to U.S. Plant Patent for a plant derived from the same breeding program that are entitled *Coreopsis* Plant Named 'Berry Chiffon' (U.S. Plant Pat. No. 27,414) and *Coreopsis* Plant Named 'Razzle Dazzle' (U.S. Plant Pat. No. 27,412).

BACKGROUND OF THE INVENTION

The present invention relates to a new and distinct cultivar of *Coreopsis* plant, botanically of hybrid origin and known as *Coreopsis* 'Sweet Tart' and will be referred to hereinafter by its cultivar name, 'Sweet Tart'. The new cultivar of *Coreopsis* is an herbaceous perennial grown for landscape and container use.

The new Invention arose from an ongoing controlled breeding program in New Braintree, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 5 in a wide range of flower colors and plant forms that do not require vernalization to intiate flowering.

The Inventor made a controlled cross in August of 2015 in New Braintree, Mass. between an unnamed and unpatented proprietary plant from his breeding program as the female parent and pollen that was pooled from a variety of unnamed and unpatented proprietary plants from his breeding program as the male parent. The exact characteristics of the pollen parent are therefore unknown. 'Sweet Tart' was selected in September of 2016 as a single unique plant amongst the resulting seedlings.

Asexual propagation of the new cultivar was first accomplished by stem cuttings under the direction of the Inventor in Kensington, Conn. in September of 2016. Asexual propagation by stem cuttings has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Sweet Tart' as a unique cultivar of *Coreopsis*.

1. 'Sweet Tart' exhibits a sturdy, well-branched plant habit reaching an average of 40 cm in height and 70 cm in width.
2. 'Sweet Tart' exhibits a floriferous and long blooming season of nearly sterile inflorescences that do not require deadheading; bloom commences in early July and lasts until frost in Kensington, Conn.
3. 'Sweet Tart' exhibits medium sized inflorescences with ray florets that are vibrant raspberry rose in color with a small area of yellow at the base (insignificant eye zone).
4. 'Sweet Tart' exhibits resistance to powdery mildew (*Podosphaera macularis*) and leafspot (*Pseudomonas cichorii*).
5. 'Sweet Tart' exhibits cold hardiness at least to U.S.D.A. Zone 5a.

The female parent of 'Sweet Tart' differs from 'Sweet Tart' in having inflorescences with ray florets that are solid dark pink in color, in not being reliably hardy in U.S.D.A. Zone 5 and in having a taller in plant height and more upright plant habit. 'Sweet Tart' can be most closely compared to *Coreopsis* cultivars 'Berry Chiffon' and 'Razzle Dazzle'. 'Berry Chiffon' and 'Razzle Dazzle' are both similar to 'Sweet Tart' in having inflorescences that are in the purple to rose color ranges, thread-like foliage and cold hardiness. 'Berry Chiffon' differs from 'Sweet Tart' in having ray florets that are primarily creamy white with a plum color eye zone. 'Razzle Dazzle' differs from 'Sweet Tart' in having ray florets that are white with a bright purple eye zone.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Publications derived directly or indirectly from the Inventor include but are not limited to website listings by Emerald Cost Growers, The Ivy Farm, Santa Rosa Gardens, and a facebook photo posted by P. Allen Smith.

BRIEF DESCRIPTION OF THE DRAWINGS

The accompanying colored photographs illustrate the overall appearance and distinct characteristics of the new *Coreopsis*. The photographs were taken of a 4-month-old plant of 'Sweet Tart' as grown outdoors in a one-gallon container from a 30-cell plug in Kensington, Conn.

The photograph in FIG. 1 provides a side view of 'Sweet Tart' and shows the plant habit in bloom.

Figure 1:
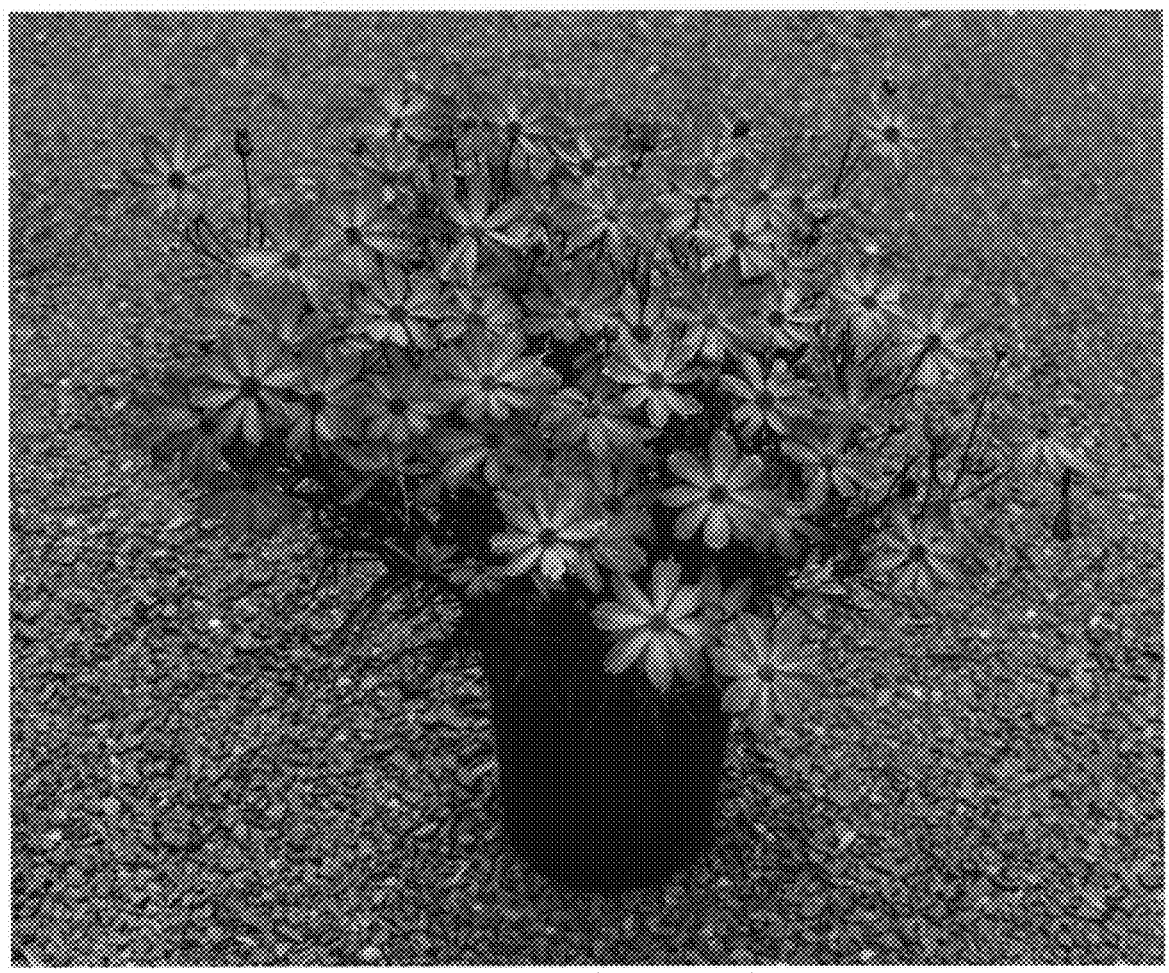
Figure 2:
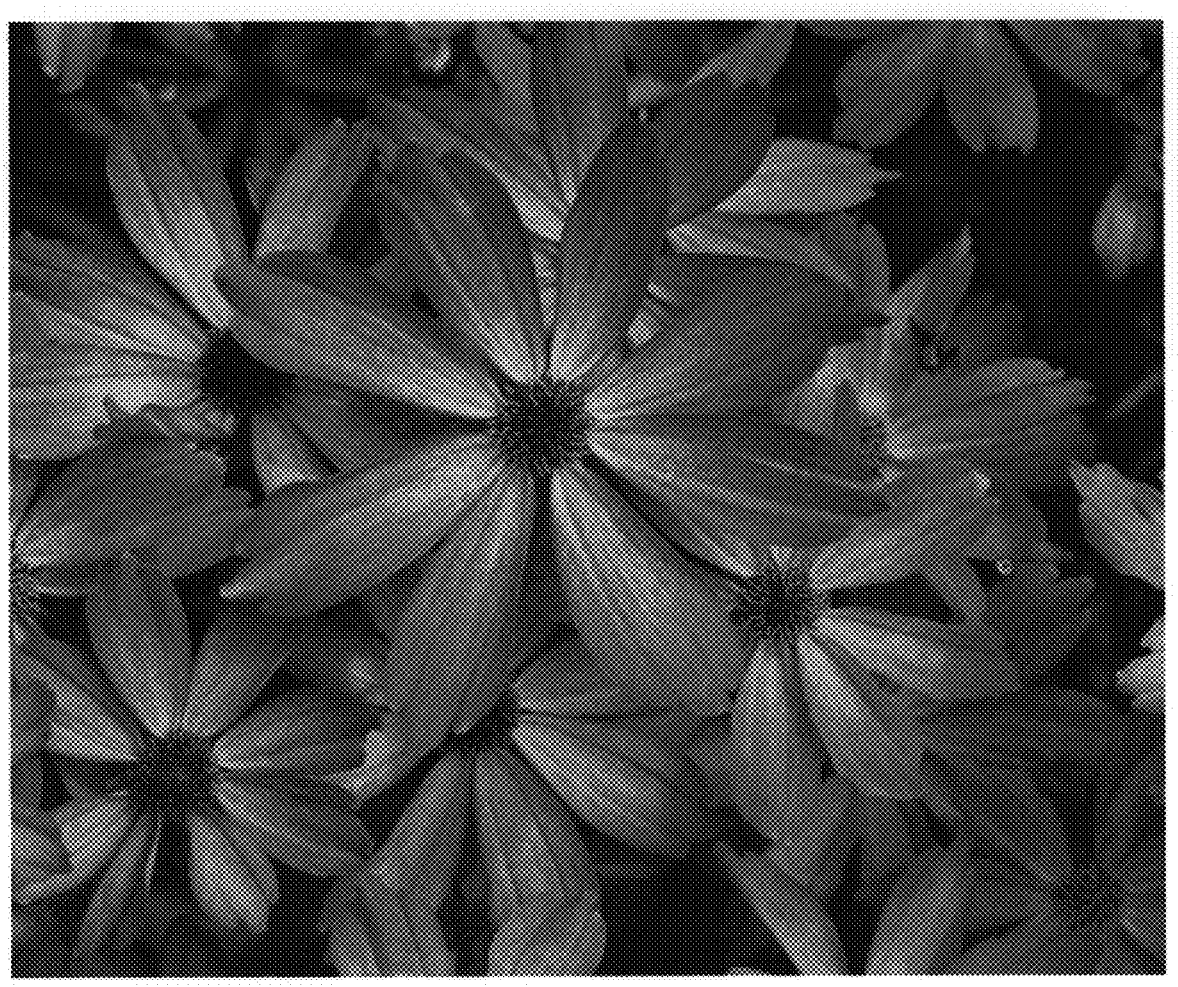

The photograph in FIG. 2 provides a close-up view of the inflorescences of 'Sweet Tart'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 4-month-old plants of 'Sweet Tart' as grown outdoors in one-gallon containers from a 30-cell plug in Kensington, Conn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Blooms from early July until frost in Kensington, Conn.

*Plant type.*—Herbaceous perennial.

*Plant habit.*—Clump-forming, compact, upright leafy flowering stems with inflorescences held above the foliage.

*Height and spread.*—Reaching an average of 37 cm in height and 30 cm in width, mature plant averages 40 cm in height and 70 cm in width as grown in the landscape.

*Cold hardiness.*—At least to U.S.D.A Zone 5a.

*Diseases and pests.*—Resistance to powdery mildew (*Podosphaera macularis*) and leafspot (*Pseudomonas cichorii*, no susceptibility or resistance to pests has been observed.

*Root description.*—Fibrous and fine, NN155A in color.

*Propagation.*—Stem cuttings.

*Root development.*—Roots initiate in 6 to 8 days and fully develop in a 128-cell plug in about 28 days with bottom heat and rooting hormone at optimal times of the year.

*Growth rate.*—Vigorous.

Stem description:

*Shape.*—Rounded to tetragonal, solid.

*Stem color.*—146A.

*Stem strength.*—Strong.

*Stem size*—Main stems; an average of 5 cm in length and 5 mm in width, lateral stems; an average of 13 cm in length (excluding peduncles) and 3 mm in width.

*Stem surface.*—Glabrous, smooth, and dull.

*Branching habit.*—Freely branched, an average of 2 basal main stems, lateral stems typically branched as oppositely arranaged pairs at each node, with an average of 4 lateral stems (2 pairs) per main stem.

*Internode length.*—An average of 3 cm.

Foliage description:

*Leaf division.*—Simple.

*Leaf margins.*—Entire, bi-fid and trifid.

*Leaf size.*—Entire leaves; an average of 7 cm in length and 8 cm in width, trifid leaves; center lobe an average of 6 cm in length and 3 mm in width, lateral lobes an average of 4 cm in length and in 2 mm width.

*Leaf shape.*—Narrow obanceolate.

*Leaf base.*—Cuneate.

*Leaf apex.*—Bluntly acute.

*Leaf venation.*—Pinnate, inconspicuous, same color as leaf.

*Leaf attachment.*—Sessile.

*Leaf arrangement.*—Opposite.

*Leaf surface.*—Upper and lower surfaces; dull, smooth, and glabrous.

*Leaf color.*—Young and mature upper and lower surface; 146A.

Flower description:

*Inflorescence type.*—Composite with a single row of ray florets surrounding disk florets in the center, forming a radiant head, inflorescences are borne on branch terminals in loose corymbs.

*Lastingness of inflorescence.*—8 to 10 days until senescence of ray flowers, phyllarys and disk flowers are persistent.

*Fragrance.*—Very faint pleasant scent.

*Quantity of inflorescences.*—Free flowering, an average of 4 corymbs per main branch, an average of 2 composites per corymb.

*Inflorescence size.*—Corymbs; an average of 15 cm in length and 9 cm in width, composite; an average of 2 cm in depth and 6 cm in diameter with disk portion up to 1 cm in diameter.

*Inflorescence buds.*—Globose in shape, an average of 4 mm in depth and diameter, smooth and shiny surface; color; a blend of 146A at base, 165B and 10A at the top.

*Peduncle.*—Rounded in shape, strong, an average of 8 cm in length and 1 mm in diameter, 146A in color, smooth and glabrous surface.

Phyllaries (involucral bracts):

*Phyllary number.*—2 rows; outer (lower) row 8, inner (upper) row 8.

*Phyllary arrangement.*—Outer (lower) phyllaries; 10% fused, held horizontal to slightly upwards with the apex and mid-section recurved downwards, inner (upper) phyllaries; overlap and surround receptacle with apical portion reflexed (campanulate-like).

*Phyllary size.*—Outer (lower) phyllaries; an average of 3 mm in length and 1 mm in width, inner (upper) phyllaries; an average of 8 cm in length and 3 mm in width.

*Phyllary color.*—Upper and lower surfaces, outer (lower) phyllaries; 146A, margins 145B, inner (upper) phyllaries; transluscent, a blend of 146A and 13A.

*Phyllary texture.*—Outer (lower) phyllaries; glabrous and smooth on both surfaces, inner (upper) phyllaries; glabrous and slightly waxy on both surfaces.

*Phyllary apex.*—Acute.

*Phyllary base.*—Truncate.

*Phyllary shape.*—Outer (lower) phyllaries; elliptic to lanceolate, inner (upper) phyllaries; lanceolate.

Ray florets (sterile):

*Number.*—8.

*Shape.*—Oblanceolate, with the appearance of 3 longitudinal sections.

*Size.*—An average of 2.1 cm in length and 1 cm in width.

*Apex.*—Rounded with rounded lobes.

*Base.*—Cuneate.

*Margins.*—Entire on sides with lobed and notched apex.

*Aspect.*—Held mainly horizontal and slightly upwards, perpendicular to peduncle.

*Texture.*—Both surfaces; glabrous, dull, and satiny.

*Color.*—Upper and lower surfaces when opening; a blend of 1A, 10A, 14A, and 64A, upper and lower surface when fully open; a blend of 20C and 64A, 14A at the base, as the flower matures upper surface turning to a blend of 20C and 71A and 71B, 14A at the base, mature lower surface; a blend of 11B, 16A and 71A with 71A mainly on the margins.

Disk florets (male and female):

*Number.*—An average of 100.

*Shape.*—Tubular, corolla is fused, flared and slightly curled at apex.

*Size.*—About 6 mm in length and 0.5 mm in width.

*Color.*—En masse; a blend of 200A and 14A, corolla; (tube) base and mid-section transluscent, 142A, flushed with 24A, top below flare 24A, flared portion 24A.

*Receptacle.*—An average of 6 mm in diameter and 3 mm in depth, 142A in color.

Reproductive organs:

*Presence.*—Disk flowers only.

*Gynoecium.*—1 Pistil; an average of 5 mm in length, style; very fine and N167A in color, bifid pillose, stigma; 14A in color with recurved branches about 1 mm in length, ovary is inferior, oblong in shape, an average of 2 mm in length and 1 mm in width, and 142A in color.

*Androecium.*—4 stamens, fused into tube surrounding style, an average of 3 mm in length and less than 0.5 mm in width, 202A in color, no pollen was present.

*Seed.*—Seed development has been observed to be very minimal; nearly sterile, plants available for data collection did not set seed.

It is claimed:

1. A new and distinct cultivar of *Coreopsis* plant named 'Sweet Tart' as herein illustrated and described.

* * * * *